United States Patent
Kaestle (10) Patent No.: US 10,110,859 B2
(45) Date of Patent: Oct. 23, 2018

(54) SYSTEM, METHOD AND DEVICE FOR MONITORING LIGHT AND SOUND IMPACT ON A PERSON

(71) Applicant: KONINKLIJKE PHILIPS N.V., Eindhoven (NL)

(72) Inventor: Siegfried Walter Kaestle, Nuffringen (DE)

(73) Assignee: Koninklijke Philips N.V., Eindhoven (NL)

( * ) Notice: Subject to any disclaimer, the term of this patent is extended or adjusted under 35 U.S.C. 154(b) by 222 days.

(21) Appl. No.: 14/892,321

(22) PCT Filed: Jun. 2, 2014

(86) PCT No.: PCT/EP2014/061316
§ 371 (c)(1),
(2) Date: Nov. 19, 2015

(87) PCT Pub. No.: WO2014/198570
PCT Pub. Date: Dec. 18, 2014

(65) Prior Publication Data
US 2016/0112681 A1 Apr. 21, 2016

Related U.S. Application Data

(60) Provisional application No. 61/833,475, filed on Jun. 11, 2013.

(30) Foreign Application Priority Data

Jun. 11, 2013 (EP) ..................... 13171351

(51) Int. Cl.
*H04N 7/18* (2006.01)
*A61B 5/11* (2006.01)
(Continued)

(52) U.S. Cl.
CPC .......... *H04N 7/183* (2013.01); *A61B 5/0077* (2013.01); *A61B 5/11* (2013.01); *A61B 5/165* (2013.01);
(Continued)

(58) Field of Classification Search
CPC .... A61B 2560/0242; A61B 2560/0443; A61B 5/0077; A61B 5/11; A61B 5/165;
(Continued)

(56) References Cited

U.S. PATENT DOCUMENTS 5,971,913 A * 10/1999 Newkirk ................ A61G 11/00
600/22
6,409,654 B1 * 6/2002 McClain ................ A61G 11/00
600/22

(Continued)

FOREIGN PATENT DOCUMENTS

| EP | 2278507 A2 | 1/2011 |
| GB | 2399928 A | 9/2004 |

(Continued)

OTHER PUBLICATIONS

Verkruysse et al, Remote Plethysmographic Imaging Using Ambient Light, XP-055065281, Optics Express, vol. 16, No. 26, 2008, pp. 21434-21445.

(Continued)

*Primary Examiner* — Thai Q Tran
*Assistant Examiner* — Stephen R Smith (57) ABSTRACT

The present invention relates to a system for monitoring light and sound impact on a patient. It comprises a light capturing unit (2) for capturing ambient light at the person over time and a sound capturing unit (3) for capturing ambient sound at the person over time. A threshold unit (6, 9) generates and issues a trigger signal if the brightness of captured ambient light exceeds a brightness level and/or if (Continued)

the sound level of captured ambient sound exceeds a sound threshold. A stress level processor (15) determines the stress level of the person. A storing unit (10) stores, in response to a received trigger signal, snippets of ambient light and ambient sound captured around the time moment of receiving the trigger signal and snippets of stress level information of the person around the time moment of receiving the trigger signal. A review unit (11) is provided to review stored snippets of ambient light, ambient sound and stress level information allowing to identify the root cause of the ambient light and ambient sound stored in a reviewed snippet and to derive guidance information indicating how to avoid such light and/or sound caused by an identified root cause.

15 Claims, 2 Drawing Sheets (51) Int. Cl.

| | | |
|---|---|---|
| *G06F 19/00* | (2018.01) | |
| *A61B 5/00* | (2006.01) | |
| *A61B 5/16* | (2006.01) | |
| *G06K 9/00* | (2006.01) | |
| *G06K 9/32* | (2006.01) | |
| *G06K 9/46* | (2006.01) | |
| *G08B 21/18* | (2006.01) | |
| *H04N 5/77* | (2006.01) | |
| *G16H 50/20* | (2018.01) | |

(52) U.S. Cl.
CPC .......... *G06F 19/00* (2013.01); *G06F 19/3418* (2013.01); *G06K 9/00604* (2013.01); *G06K 9/3233* (2013.01); *G06K 9/4661* (2013.01); *G08B 21/182* (2013.01); *G16H 50/20* (2018.01); *H04N 5/77* (2013.01); *A61B 2560/0242* (2013.01); *A61B 2560/0443* (2013.01)

(58) Field of Classification Search
CPC .............. G06F 19/3418; G06F 19/345; G06K 9/00604; G06K 9/3233; G06K 9/4661; G08B 21/182; H04N 5/77; H04N 7/183
USPC .............. 348/77, 78; 600/22, 301, 407, 473
See application file for complete search history.

(56) References Cited

U.S. PATENT DOCUMENTS

| | | | |
|---|---|---|---|
| 2002/0183947 A1 | 12/2002 | Ando et al. | |
| 2005/0215845 A1* | 9/2005 | Mahony | A61B 5/02055 600/22 |
| 2007/0241911 A1 | 10/2007 | Swan et al. | |
| 2008/0082019 A1* | 4/2008 | Ludving | A61B 5/04004 600/544 |
| 2008/0292151 A1* | 11/2008 | Kurtz | A61B 3/10 382/128 |
| 2009/0005657 A1 | 1/2009 | Bodlaender et al. | |
| 2010/0217099 A1* | 8/2010 | LeBoeuf | A61B 5/00 600/301 |
| 2011/0311119 A1* | 12/2011 | Jeanne | G06T 7/20 382/128 |
| 2012/0157757 A1 | 6/2012 | Ten Eyck et al. | |
| 2012/0157796 A1 | 6/2012 | Ten Eyck et al. | |
| 2012/0257051 A1 | 10/2012 | Cheng et al. | |
| 2013/0182107 A1* | 7/2013 | Anderson | G08B 21/02 348/143 |
| 2014/0035807 A1* | 2/2014 | Lee | G06K 9/4661 345/156 |
| 2014/0088433 A1* | 3/2014 | Shan | A61B 5/1128 600/473 |

FOREIGN PATENT DOCUMENTS

| | | |
|---|---|---|
| JP | 2007276766 A | 10/2007 |
| RU | 2392860 C1 | 6/2010 |
| RU | 2466677 C1 | 11/2012 |
| WO | 02062282 A1 | 8/2002 |
| WO | 2009073396 A1 | 6/2009 |
| WO | 2012082297 A2 | 6/2012 |
| WO | 2013027027 A2 | 2/2013 |

OTHER PUBLICATIONS

Anonymous, "UFOCaptureV2 Users Manual Index", sonota.com, retrieved from URL:http://sonotaco.com/soft/uf02/help/english/index.html, 2013, 43 Pages.

Coughlin et al, Core Measures for Developmentally Supportive Care in Neonatal Intensive Care Units: Theory, Precedence and Practice, Journal of Advanced Nursing, 2009, pp. 1-10.

Cone et al, "Single-Family Room Design in the Newborn Intensive Care Unit", Developmental Care of Newborns and Infants: A Guide for Health Professionals, Chapter 6, Undated, pp. 94-103.

Anonymous, "Soundear II, The Sound of a Good Working Environment!", Retrieved From http://soundear.com/noise-monitoring-equipment-and-noise-level-measurement/noise-monitoring-equipment-for-hospitals.html 2012, 2 Page Document.

Ulrich et al, "A Review of the Research Literature on Evidence-Based Healthcare Design", Healthcare Leadership, White Paper Series 5 of 5, 2008, pp. 1-75.

Rullo et al, "End-User Composition and Re-use of Technologies in the Neonatal Intensive Care Unit", IEEE IET Electronic Library Conferences, 2006, pp. 1-10.

* cited by examiner

SYSTEM, METHOD AND DEVICE FOR MONITORING LIGHT AND SOUND IMPACT ON A PERSON

CROSS-REFERENCE TO PRIOR APPLICATIONS

This application is the U.S. National Phase application under 35 U.S.C. § 371 of International Application No. PCT/EP2014/061316, filed on Jun. 2, 2014, which claims the benefit of U.S. Provisional Patent Application No. 61/833,475, filed on Jun. 11, 2013 and European Patent Application No. 13171351.3, filed on Jun. 11, 2013. These applications are hereby incorporated by reference herein.

FIELD OF THE INVENTION

The present invention relates a system, method and device for monitoring light and sound impact on a person, in particular a patient such as a premature baby.

BACKGROUND OF THE INVENTION

Excessive light and acoustic noise have been identified as major causes that hinder optimum development of premature babies. Baby's sleep cycle needs to be protected which is often in conflict with care giver's and visitor's schedules who create noise by talking and work. Life supporting and patient monitoring equipment all create noise by audible alarms and other sounds.

WO 2012/082297 A2 discloses a system for monitoring the physiological conditions of an infant includes an infant microenvironment. A motion sensor is disposed about the microenvironment. A processor is communicatively connected to the motion sensor. The processor receives motion signals from the motion sensors and processes the motion signals to derive an indication of a stress level of the infant. A method of monitoring the physiological condition of an infant includes detecting motion of the infant with motion sensors. A baseline motion for the infant is derived from the detected motion with a processor. An onset or change in at least one auxiliary parameter is monitored with an auxiliary sensor. Motion of the infant is monitored with the motion sensor after the onset or change in the at least one auxiliary parameter. A stress level of the infant is derived with the processor from the monitored motion of the infant.

SUMMARY OF THE INVENTION

It is an object of the present invention to provide an improved system, method and device for monitoring light and sound impact on a person.

In a first aspect of the present invention a system for monitoring light and sound impact on a person is presented that comprises
 a light capturing unit for capturing ambient light at the person over time,
 a sound capturing unit for capturing ambient sound at the person over time,
 a stress level processor for determining the stress level of the person,
 a storing unit for storing, in response to a received trigger signal, snippets of ambient light and ambient sound captured around the time moment of receiving the trigger signal and snippets of stress level information of the person around the time moment of receiving the trigger signal,—a review unit for reviewing stored snippets of ambient light, ambient sound and stress level information allowing to identify the root cause of the ambient light and ambient sound stored in a reviewed snippet and to derive guidance information indicating how to avoid such light and/or sound caused by an identified root cause.

In a further aspect of the present invention a corresponding device, e.g. in the form of a processor or computer, which may be used as part of the disclosed system, for monitoring light and sound impact on a person is presented that comprises
 a threshold unit for generating and issuing a trigger signal if the brightness of captured ambient light captured of the person over time exceeds a brightness level and/or if the sound level of ambient sound captured of the person over time exceeds a sound threshold,
 a stress level processor for determining the stress level of the person,
 a storing unit for storing, in response to a received trigger signal, snippets of ambient light and ambient sound captured around the time moment of receiving the trigger signal and snippets of stress level information of the person around the time moment of receiving the trigger signal,—a review unit for reviewing stored snippets of ambient light, ambient sound and stress level information allowing to identify the root cause of the ambient light and ambient sound stored in a reviewed snippet and to derive guidance information indicating how to avoid such light and/or sound caused by an identified root cause.

In still further aspects of the present invention corresponding methods for monitoring light and sound impact on a person are presented.

In yet further aspects of the present invention, there are provided a computer program which comprises program code means for causing a computer to perform the steps of the methods disclosed herein when said computer program is carried out on a computer as well as a non-transitory computer-readable recording medium that stores therein a computer program product, which, when executed by a computer, causes the methods disclosed herein to be performed.

Preferred embodiments of the invention are defined in the dependent claims. It shall be understood that the claimed device, methods, computer program and medium have similar and/or identical preferred embodiments as the claimed system and as defined in the dependent claims.

The present invention is based on the idea to monitor and track illumination and sound levels by corresponding light capturing means and sound capturing means, respectively, e.g. by use of a standard web cam with microphone, to provide the necessary support to identify and minimize causes of these noxious stimuli for the monitored person. The obtained measurements are recorded using captured (raw) sound and light data snippets to identify root causes of loud and flashing events that should be eliminated or avoided to remove or at least reduce the impact of light and sound to the monitored person.

The monitored persons that shall preferably be protected from such noxious stimuli may e.g. be infants, newborns or premature babies, and the present invention may give caregivers the necessary support. Modern neonatal intensive care units (NICUs) are taking care of these effects by applying the so-called developmental care model which is further supported by the present invention. Other monitored persons are patients in a hospital, in particular in an intensive care unit (ICUs), elder people or, generally, all people who are very sensitive to noise and/or light and who need special attention and protection from those noise and/or illumination events.

In an embodiment said light capturing unit comprises a camera, for instance a video camera or web cam, for capturing images, in particular video data, of a recording area including at least the eyes of the person, when the person is located in a predetermined standard position. Particularly the eye region of the person is of interest since it reflects the impact of light that shall be checked if it exceeds a predetermined threshold (brightness level). However, it may also be possible to capture images of the whole face, head or even the whole body of the person or the area where the person is normally placed (e.g. a bed of a patient or an incubator of a premature baby). For the evaluation a region of interest (preferably including the eyes of the person) may be selected, for instance after segmentation of the images. The images are generally recorded continuously, but may also be recorded at intervals.

In a preferred embodiment the system further comprises an overview camera for capturing overview images, in particular video data, of the environment of the person, wherein the storing unit is configured to store in response to a received trigger signal, a snippet of overview images captured around the time moment of receiving the trigger signal, and wherein the review unit is configured to allow reviewing stored snippets of overview images in addition to stored snippets of ambient light and ambient sound to identify the root cause of the ambient light and ambient sound stored in a reviewed snippet. This improves the identification of excessive sound and light events since the events may be visually recognizable on the recorded overview images and may even help to identify the root causes that would otherwise not have been recognizable.

Preferably the review unit is configured to automatically review stored snippets of overview images in addition to stored snippets of ambient light and ambient sound to identify the root cause of the ambient light and ambient sound stored in a reviewed snippet.

For instance, in an embodiment the stored snippets of ambient light and/or ambient sound may be compared to a database storing earlier recorded snippets for which the root causes are already known, e.g. from an earlier detection. Thus, the system may be a self-learning system, in which identified root causes and the associated snippets of sound and/or light are recorded in the database for later identification.

Advantageously, the review unit is configured to review stored snippets of ambient light and ambient sound to identify the root cause of the ambient light and ambient sound stored in the snippet and to derive guidance information indicating how to avoid such light and/or sound caused by an identified root cause. For this purpose statistical measures, (sound and/or light) recognition means, image recognition means, movement pattern recognition means etc. may be used.

Such guidance information may include instructions for caregiver what to do and what to avoid near the monitored person, which devices to use or not to use, etc. These instructions may be used as training material for training of new personnel or for a regular update on behavioral rules of the personnel, e.g. to support the developmental care model.

In another embodiment the system further comprises a sound processor for processing captured ambient sound before checking if the sound level of captured ambient sound exceeds a sound threshold by the threshold unit by applying a weighting representing the spectral human hearing sensitivity, in particular the spectral hearing sensitivity of a person comparable to the monitored person. This further improves the accuracy of the monitoring and avoids false recognitions of noise events that are, in fact, not negative for the person, or, on the other hand, ensures that really negative noise events are reliably recognized.

A similar improvement with respect to the reliable recognition of light events is achieved by further providing a light processor that is configured to process captured images before checking if the light level of a captured images exceeds a light threshold by the threshold unit by applying a weighting representing the human eye sensitivity, in particular the eye sensitivity of a person comparable to the monitored person.

In another embodiment the system further comprises an image processor for processing captured images before checking if the light level of a captured images exceeds a light threshold by the threshold unit by selecting a region of interest in an image that includes or is adjacent to the eyes of the person and by deriving a brightness measure of the region of interest by averaging the intensity of all pixels in the region of interest or selecting the intensity of the brightest pixel, wherein said brightness measure is used as light level for checking if the light level of a captured images exceeds a light threshold by the threshold unit. Again, this embodiment further improves the accuracy and reliability of the recognition of negative light events.

In another embodiment an alarm unit is provided for generating an alarm if the brightness of captured ambient light exceeds a brightness level and/or if the sound level of captured ambient sound exceeds a sound threshold. Thus, an immediate recognition of a negative event can be immediately signaled to enable an immediate reaction.

The proposed system further comprises a stress level processor for determining the stress level of the person, wherein the storing unit is configured to store in response to a received trigger signal, a snippet of stress level information of the person around the time moment of receiving the trigger signal, and wherein the review unit is configured to allow reviewing stored snippets of stress level information in addition to stored snippets of ambient light and ambient sound to identify the root cause of the ambient light and ambient sound stored in a reviewed snippet. Various kinds of sensors may be used to get sensor signals that can be used to determine the stress level of the person. Such sensors may include, but are not limited to, one or more of a heart rate sensor, a breathing rate sensor, an ECG sensor, a SpO2 sensor, a skin conductivity sensor, a skin moisture sensor, a motion sensor, etc. The sensor signals are then provided to the stress sensor processor to determine a stress level of the person. Methods for determine the stress level (also referred to as physiological condition) from such kinds of signals are generally known in the art, e.g. from the above cited WO 2012/082297 A2, WO2009/138923 A1 or WO2012/140537 A1. Knowing the stress level of the person further improves the identification of noise or light events that are really negative for the person as proven by a stress level indicating increased stress of the person, which thus also improves the generation of guidance information how to avoid or reduce such noise or light events.

Still further, in an improved embodiment said light capturing unit comprises a camera for capturing images, in particular video data, of a recording area including at least the eyes of the person, when the person is located in a predetermined standard position, wherein the system further comprises a remote photo-plethysmographic (remote PPG) processor for deriving vital signs of the person from captured images for use by the stress level processor for determining the stress level of the person using a method as commonly known and as mentioned above. Thus, advantageously a camera is not only used to capture images of the person, but the image of the person are also evaluated to derive vital signs (in particular breathing rate, heart rate, SpO2) according to the known principles of remote PPG. Such principles and the derivation of vital signs are e.g. described by Verkruysse et al., "Remote plethysmographic imaging using ambient light", Optics Express, 16(26), 22 Dec. 2008, pp. 21434-21445 who demonstrates that photoplethysmographic signals can be measured remotely using ambient light and a conventional consumer level video camera, or by Wieringa, et al., "Contactless Multiple Wavelength Photoplethysmographic Imaging: A First Step Toward "SpO2 Camera" Technology," Ann. Biomed. Eng. 33, 1034-1041 (2005), who discloses a remote PPG system for contactless imaging of arterial oxygen saturation in tissue based upon the measurement of plethysmographic signals at different wavelengths. Vital signs obtained in this way can then again be used, potentially in combination with other sensor signals, to determine the stress level of the person.

In a further embodiment the system further comprises a patient support for supporting the person, in particular a bed, a crib, an infant warmer or an incubator, wherein the person is a patient, an infant or a newborn. For instance, the person (e.g. a premature baby) is located in a microenvironment such as an incubator in which (or at least close to which) the light capturing unit and the sound capturing unit are arranged.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
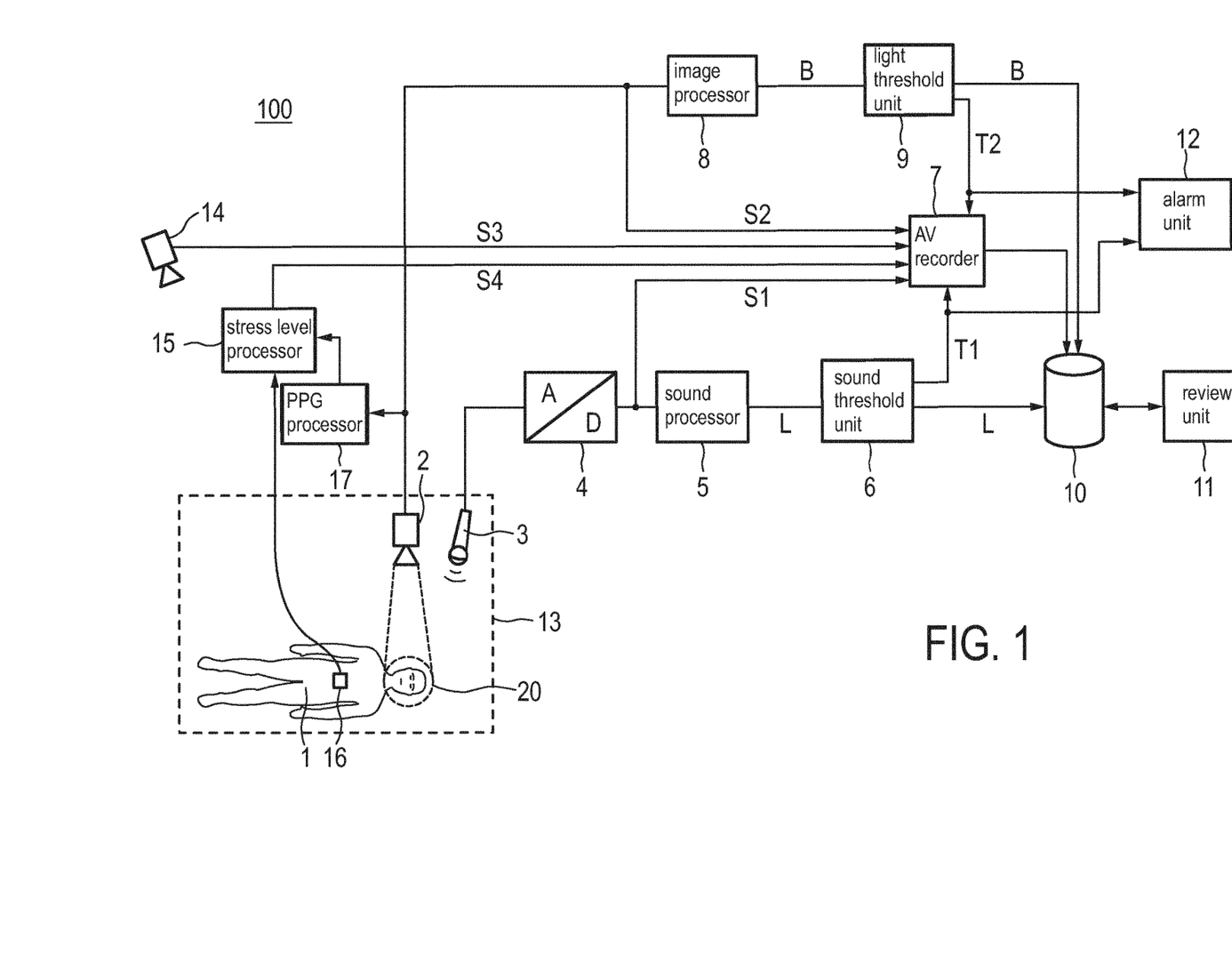
FIG. 1 shows a schematic diagram of an embodiment of a system for monitoring light and sound impact on a person according to the present invention.

FIG. 1 shows a schematic diagram of an embodiment of a system 100 for monitoring light and sound impact on a person according to the present invention. The person, here a baby 1, is located in this embodiment in an open environment like a bed, crib or infant warmer unit or in a closed incubator 13 (sometimes also referred to a microenvironment of the baby). A video camera 2 and a microphone 3 (favorably included in the video camera 2) are located close to the baby 1 in order to capture ambient sound and ambient light that is relevant to the baby's senses.

In case of an incubator 13 this means that the microphone 3 is preferably arranged inside or at least acoustically connected to the inside of the incubator 13 in order to measure the relevant sounds. On one hand there may additional noise be created by the impeller and heating system of the incubator 13 and noise by opening and closing of the incubator doors that matters for the baby, but on the other hand, the incubator walls shield from ambient room noise, i.e. it may dependent of those other noise sources whether to arrange the microphone 3 inside or outside of the incubator 13.

The camera 2 is preferably arranged outside of the incubator 13 as long as it has vision to the baby 1. The images captured by the camera 2 preferably include at least the eyes or the head of the baby 1 as this matter for light impact. In case of a fixed mounting of a camera 2 it is generally directed to a recording area 20 including at least the eyes or the head of the person, when the person is located in a predetermined standard position (as shown in FIG. 1). Since the baby 1 may move, in a preferred embodiment the camera 2 is preferably movable as well, e.g. by mechanically moving or swiveling the camera or by changing the viewing angle and thus the recording area 20, depending on the position of the head or eyes of the baby. For this purpose the captured images may be used to recognize the position of the baby 1 and thus to control the camera 2 accordingly. In another embodiment the viewing angle of the camera may be made larger if the eyes or face of the baby 1 are no longer visible in the images.

In an open system the position of the camera 2 and microphone 3 does not matter as much, but proximity to the baby 1 is useful to capture sound and light levels representative to the signals reaching the baby's eyes and ears.

Following the audio path an amplification-and-AD unit 4 is provided for amplifying and AD (analog-to-digital) converting the captured audio signals. Its output feeds an (optional) sound processor 5 and an audio-video (AV) recorder 7.

The sound processor 5 preferably processes the raw audio wave data covering the typical hearing frequency range (20 Hz to 20000 Hz). It may derive typical parameters known in the field of noise monitoring like equivalent continuous sound pressure level $L_{ep}$, limit levels like $L_{10}$ (10% of time the noise exceeds $L_{10}$), median level $L_{50}$ and similar parameters of interest. The sound processor 5 may also allow applying a weighting curve (or weighting function) like the A-curve that is used in noise monitoring standards to represent human hearing sensitivity over the frequency band. It is understood that any other weighing function may be applied that better represents the noise strain to the respective person 1 that is monitored (here in this example a premature baby). While the A-curve is widely accepted for adult noise emission impact the A-curve may not be the optimal curve for a baby for which a more suitable function is preferably applied.

The system 100 further comprises a sound threshold unit 6 (also called sound threshold detector), e.g. implemented in a sound post-processor, that creates a sound trigger signal T1 if the sound level exceeds a predetermined (e.g. user definable) sound threshold. Said sound trigger signal T1 causes the AV recorder to record a snippet S1 of sound data (more generally: ambient sound) and a snippet S2 of video data (more generally: ambient light) around that trigger event, i.e. snippets of sound data and video data captured by the camera 2 and the microphone 3, respectively, around the time moment of receiving the sound trigger signal T1. Said snippets S1, S2 are preferably stored along with the trigger event (i.e. the sound trigger signal T1) in a trend database 10 (generally a storing unit) for later review and use, as will be explained below.

The output of the sound processor 5 is preferably a continuous sound measure L, e.g. in the form of one or more of the above mentioned typical parameters known in the field of noise monitoring like $L_{eq}$, $L_{10}$ $L_{50}$ or similar parameters of interest. The sound measure L is, directly or via the sound threshold unit 6 (as shown in FIG. 1), stored in the database 10 for trending and later review. Continuous recording of sound is, however, not mandatory; at minimum, snippets of sound records and associated sound measures L are used to classify the intensity of the event. In still another embodiment only light is monitored and recorded, but no sound.

Following the video path an (optional) image processor 8 is provided for processing the captured image data. In an embodiment the image processor 8 is configured to pick a region of interest (ROI) from the complete video frame that includes or is as close as possible to the eyes of the baby 1 in order to match the light strain to the baby 1. In a further embodiment it averages the intensity of all the pixels in the ROI to derive a brightness measure. For instance, the brightest spot in the ROI may be used as an indication of brightness.

The camera 2 could be a standard RGB camera giving three color frames at a time, a monochrome camera with just one detector or a special camera with multiple detectors at wavelengths determined by dedicated filters. In case of various color components like RGB they could be weighted and added to create a single output brightness image and overall value. Similar to the above explained sound processor 5 the weighting function (luminosity function) is preferably selected to represent human eye sensitivity leading to perceived illumination levels as measured in lux. It is understood that any other weighting scheme may be applied that is better related to the optical strain of the monitored persons, e.g. on a premature baby 1 in this example.

In order to normalize ("calibrate") the ambient light reflections from the ROI a (white or grey) reference tag (optical standard) may be positioned in the ROI in a preferred embodiment. This could be desirable to eliminate the impact of skin color or other objects in the ROI when estimating incident light intensity and make the measurement more accurate to match light meter results.

The system 100 further comprises a light threshold unit 9 (also called light threshold detector), e.g. implemented in an image post-processor, that creates a light trigger signal T2 if the light level exceeds a predetermined (e.g. user definable) light threshold.

Similar to the sound trigger signal T1, said light trigger signal T2 causes the AV recorder to record a snippet S1 of sound data (more generally: ambient sound) and a snippet S2 of video data (more generally: ambient light) around that trigger event, i.e. snippets of sound data and video data captured by the camera 2 and the microphone 3, respectively, around the time moment of receiving the sound trigger signal T2. Said snippets S1, S2 are preferably stored along with the trigger event (i.e. the light trigger signal T1) in a trend database 10 (generally a storing unit) for later review and use, as will be explained below.

The output of the light processor 8 is preferably a continuous brightness measure B as luminous emittance ($M_v$) or illuminance ($E_v$) or a non-standard definition. The intensity stream B is, directly or via the light threshold unit 9 (as shown in FIG. 1), stored in the database 10 for trending and later review. Continuous recording of light is, however, not mandatory; at minimum, snippets of light recordings and associated brightness measures B are used to classify the intensity of the light. In still another embodiment only sound is monitored and recorded, but no light.

In the preferred embodiment the system 100 as shown in FIG. 1 both the sound threshold unit 6 and the light threshold unit 9 are present and both units can generate a corresponding trigger signal causing the AV recorder 7 to record snippets of captured light and sound around the trigger event in the database 10. However, in other embodiments only the threshold unit 6 or the light threshold unit 9 is present and can generate a corresponding trigger signal.

The system 100 preferably comprises an alarm unit 12 (e.g. a flashing light, a red lamp, a loudspeaker, etc.) that is configured or can be programmed to create visual and/or audible alarms if a light threshold or a sound intensity threshold is exceeded. The alarm unit 12 is preferably triggered by one of the trigger signals T1, T2.

The system 100 further comprises a review unit 11 to retrospectively check the monitored levels of ambient light and sound imposed on the baby 1, i.e. to review stored snippets of ambient light and ambient sound to allow identifying the root cause of the ambient light and ambient sound stored in a reviewed snippet. Along with the snippets stored in the database 10, in a preferred embodiment the user can review the events that exceeded preset thresholds and are most likely the dominating factors of strain on the baby 1. Preferably, the original video and sound sequence are stored as well and at hand, which can further help to identify the root cause.

The review unit 11 is further configured to allow deriving guidance information indicating how to avoid such light and/or sound caused by an identified root cause. In other words, knowing the outstanding noise and light events can help train the staff and visitors in a NICU to provide better developmental care. In this way a quiet, dimly lit, private environment can be provided that promotes safety and sleep. Further, it can be ensured that continuous background sound and transient sound in the neonatal intensive care unit does not exceed an hourly continuous noise level ($L_{eq}$) of 45 decibels (dB) and an hourly $L_{10}$ (the noise level exceeded for 10% of the time) of 50 dB. Further, it can be ensured that transient sounds or $L_{max}$ (the single highest sound level) shall not exceed 65 dB. Further, ambient light levels ranging between 10-600 lux and 1-60 foot candles can be made adjustable and measured at each infant bed space.

In a more advanced embodiment the review unit 11 is configured to automatically review stored snippets of overview images in addition to stored snippets of ambient light and ambient sound to identify the root cause of the ambient light and ambient sound stored in a reviewed snippet. Thus, the identification of the causes for events of exceeding noise and/or light is automated. Preferably, the generation of guidance information based on the identification is automated as well.

For instance, in an embodiment the review unit 11 is configured such that sound and light events can be identified in real time. An (immediate) feedback can then be given to the use, for instance in clear text (e.g. "loud taking"), or even an (immediate) instruction ("guidance information") could be output (e.g. "lower voice"). For light events the feedback or the instruction could be "dim room light", "close curtain", etc. The same feedback and instructions can be generated later (i.e. not in real time) for use in the general guidance or later feedback of personnel.

For generating the guidance information both the sound recording and the light recordings (and other potentially information, e.g. video data of the room) are preferably evaluated to identify the root cause (e.g. from the video data of the room where a certain action or person doing something) can been recognized. The snippet of video data may then be included in the guidance information to tell the personnel which actions to suppress to avoid a certain sound and/or light event. Optionally, the system 100 further comprises an overview camera 14 for capturing overview images, in particular video data, of the environment of the baby 1, e.g. of the whole room including the complete incubator 13 and the area around it, maybe even including doors and windows of the room. In response to a received trigger signal T1 or T2, a snippet S3 of overview images captured around the time moment of receiving the trigger signal is stored as well so that the stored snippets S3 of overview images may be used by the review unit 11 in addition to stored snippets of ambient light and ambient sound to enable identification or to automatically identify the root cause of the ambient light and ambient sound stored in a reviewed snippet. In this way the identification of the root cause can be improved since e.g. in such overview images the origin (e.g. a certain device) or originator (e.g. a caregiver using a device making noise) of excessive noise or excessive light may be visible. This will also improve the generation of the guidance information. In a further improved system not only a single overview camera, but a plurality of overview cameras is provided in the environment of the monitored person to deliver images of different areas of the environment. Further, in an embodiment not only snippets S3 of overview images are recorded, but overview images are recorded continuously.

As a further option the system 100 may additionally comprise a stress level processor 15 for determining the stress level of the baby 1. In response to a received trigger signal T1 or T2, a snippet S4 of stress level information of the baby 1 captured around the time moment of receiving the trigger signal is then recorded in the database 10. These stored snippets S4 of stress level information may then be used by the review unit 11 in addition to stored snippets of ambient light and ambient sound to enable identification or to automatically identify the root cause of the ambient light and ambient sound stored in a reviewed snippet. This may increase the accuracy and reliability of the identification and generation of guidance information since by use of the determined stress level it can be easily verified if an excessive light or sound level indeed provided a negative effect on the monitored person or not.

For determining the stress level one or more physiological signals of the person are preferably evaluated, such physiological signals including one or more of heart rate, breathing rate, ECG, blood oxygenation, skin conductivity, a skin moisture, body motion, etc. To obtain such physiological signals dedicated sensors (as schematically indicated by a sensor 16) attached to the monitored person may be used in one embodiment.

Alternatively or in addition, at least for obtaining some of these physiological signals, image data of the camera 2 may be evaluated using the commonly principles of remote photo-plethysmography (remote PPG). For this purpose a remote photo-plethysmographic processor 17 is optionally provided in an embodiment that derives vital signs of the person from captured images (preferably of the already provided camera 2 or from an additional camera (not shown)). These vital signs (e.g. the breathing rate, the heart rate, and/or the SpO2 of the person) are then provided to the stress level processor 15 for determining the stress level of the person (with or (preferably) without other physiological signals that may be provided by one or more other sensors 16).

Briefly summarized, photo-plethysmography (PPG) is an optical measurement technique that evaluates a time-variant change of light reflectance or transmission of an area or volume of interest. PPG is based on the principle that blood absorbs light more than surrounding tissue, so variations in blood volume with every heart beat affect transmission or reflectance correspondingly. Besides information about the heart rate, a PPG waveform can comprise information attributable to further physiological phenomena such as the respiration. By evaluating the transmissivity and/or reflectivity at different wavelengths (typically red and infrared), the blood oxygen saturation can be determined.

Conventional pulse oximeters for measuring the heart rate and the (arterial) blood oxygen saturation of a subject are attached to the skin of the subject, for instance to a finger tip, earlobe or forehead. Therefore, they are referred to as 'contact' PPG devices. A typical pulse oximeter comprises a red LED and an infrared LED as light sources and one photodiode for detecting light that has been transmitted through patient tissue. Commercially available pulse oximeters quickly switch between measurements at a red and an infrared wavelength and thereby measure the transmissivity of the same area or volume of tissue at two different wavelengths. This is referred to as time-division-multiplexing. The transmissivity over time at each wavelength gives the PPG waveforms for red and infrared wavelengths. Although contact PPG is regarded as a basically non-invasive technique, contact PPG measurement is often experienced as being unpleasant, since the pulse oximeter is directly attached to the subject and any cables limit the freedom to move.

Recently, non-contact, remote PPG devices for unobtrusive measurements have been introduced. Remote PPG utilizes light sources or, in general radiation sources, disposed remotely from the subject of interest. Similarly, also a detector, e.g., a camera or a photo detector, can be disposed remotely from the subject of interest. Therefore, remote photoplethysmographic systems and devices are considered unobtrusive and well suited for medical as well as non-medical everyday applications. However, remote PPG devices typically achieve a lower signal-to-noise ratio.

In addition to evaluating the time-variant transmissivity and/or reflectivity, camera-based PPG also enables the evaluation of movements of the body of the subject. Pulsatile as well as respiratory movements can be evaluated.

This known technology has meanwhile been described in many publications and patent applications, e.g. in the above cited publications of Verkruysse et al. and of Wieringa, et al. and in patent applications WO2012/093358 A1 or WO 2013/030745 A1 (just to name a few), the content of which, particularly the explanations of the principles of remote PPG, is incorporated herein by reference.

The determination of the stress level of a person from physiological signals or vital signs, respectively, independent how they are obtained, is also generally known in the art. For instance, in WO 2012/082297 A2 an apparatus and method for measuring the user's mental stress level is described. The apparatus comprises a first measuring unit for measuring a heart rate variability (HRV) signal of a user, a second measuring unit for obtaining a respiration signal of the user, and a processing unit for generating an indicative signal representing the user's mental stress level in dependence on the obtained respiration signal and the measured HRV signal. In WO2012/140537 A1 a stress-measuring device and method for determining a level of stress of a user, in particular long-term stress, are described. The stress-measuring device comprises an input interface for receiving a skin conductance signal indicating the skin conductance of the user, the skin conductance signal over time forming skin conductance trace data. The stress-measuring device further comprises a processing unit for processing the skin conductance trace data, the processing unit adapted to determine, over at least a portion of the skin conductance trace data, values of a rise time between at least two different points of the skin conductance trace data, to determine a frequency distribution of the rise time values, and to determine the level of stress of the user based on the determined frequency distribution. These and other methods may be used according to the embodiment of the system according to the present invention comprising a stress level processor 15.

Thus, the present invention teaches how a camera with microphone (e.g. web cam) can be used in the NICU environment to monitor light and sound levels in order to support the developmental care model. Excessive light and acoustic noise has been identified as major causes that hinder optimum development of premature babies. Baby's sleep cycle needs to be protected which is often in conflict with caregiver's and visitor's schedules who create noise by talking and work. Monitoring and tracking of illumination and sound levels by a standard web cam equipment can provide caregivers the necessary support to identify and minimize causes of these noxious stimuli for premature babies.

To measure and track acoustic noise using a dedicated microphone and a display module may be used in an embodiment, but this may be achieved as well using a standard web cam approach. The built-in microphone could be calibrated and equalized to serve as low cost sound meter. Calibration or evaluation of sound levels could include using the human ear sensitivity function (A-weighting filter). For a baby a sound frequency profile as the fetus would experience in the mother's womb should serve as reference. Assuming that a fetus develops best in the womb conditions it means that higher pitch sounds are more annoying than lower pitch sounds. It is understood by the skilled person that a sound monitoring system could be normalized to any desired frequency sensitivity function.

Another advantage over standard level meters is that the web cam can track outstanding events and store snippets of video and audio together that allows retrospectively reviewing these events and identifying the source. This enables finding and eliminating the root causes of unhealthy noise and light events and improve the developmental situation of the premature baby.

Thus, a practical implementation of a proposed sound and light monitoring system comprises
 a web cam with microphone,
 a processing unit to derive sound pressure and light levels (averages) and events (peaks, threshold excursions) that are relevant for the baby;
 means for recording storage snippets of audio and video for outstanding events;
 review capabilities of history and events;
 means for automatic identification and classification of light and sound events; and
 display and alarm capabilities that may be local at the baby (immediate feedback) or at a remote central point.

Automatic identification of events could ease the review of noise and light history. Standard sound patterns like talk, baby crying, banging a door, equipment alarms etc. could detected by a capable sound recognition system. Further, sharing the video camera with microphone for other applications like vital signs monitoring avoid additional equipment in the space limited NICU.

Figure 2:
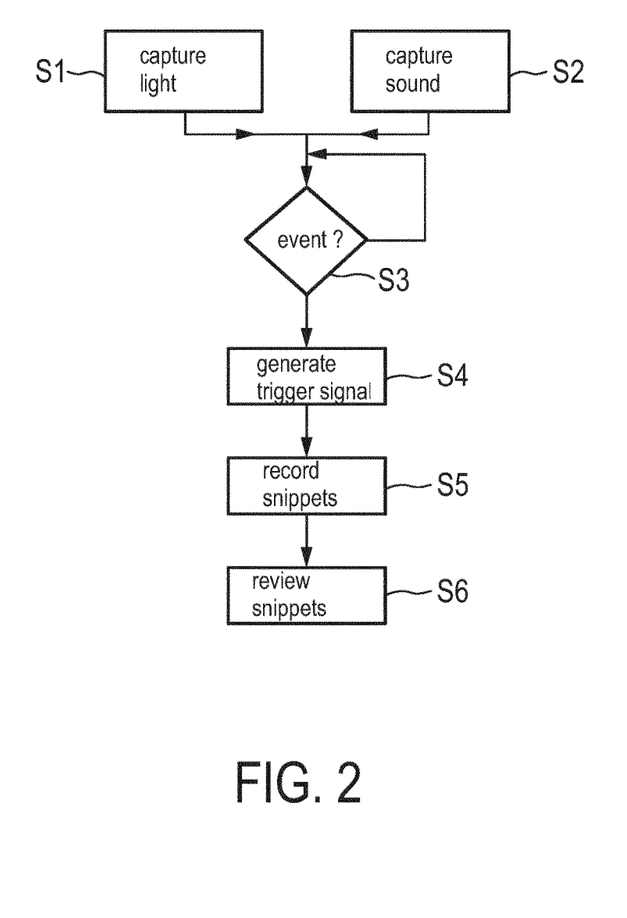
FIG. 2 shows a flow chart of an embodiment of a method for monitoring light and sound impact on a person according to the present invention.

Finally, a flow chart of an embodiment of a proposed method for monitoring light and sound impact on a person is depicted in FIG. 2. In step S1 ambient light at the person is captured over time. In parallel, in step S2, ambient sound at the person is captured over time. In step S4 a trigger signal is generated and issued if the brightness of captured ambient light exceeds a brightness level and/or if the sound level of captured ambient sound exceeds a sound threshold, which is checked in step S3. In step S5, in response to a received trigger signal, snippets of ambient light and ambient sound captured around the time moment of receiving the trigger signal are recorded. Finally, in step S6 stored snippets of ambient light and ambient sound are reviewed allowing to identify the root cause of the ambient light and ambient sound stored in a reviewed snippet and to derive guidance information indicating how to avoid such light and/or sound caused by an identified root cause.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A system for monitoring light and sound impact on a person, comprising:
 a light capturing unit configured to capture ambient light at an area where the person is located over time, wherein the light capturing unit comprises a camera configured to capture images of the area, and wherein the light capturing unit comprises one or more processors configured to determine an ambient light brightness of the captured ambient light from a segment of the image containing at least the eyes of the person;
 a sound capturing unit configured to capture ambient sound at the area where the person is located over time;
 a sound processor configured to process audio wave data from the captured ambient sound, the sound processor applying a weighting to the audio wave data based upon a spectral hearing sensitivity of a person of similar age as the monitored person;
 a threshold unit configured to generate and issue a trigger signal responsive to the brightness of the captured ambient light breaching a brightness threshold and/or responsive to a sound level of the weighted audio wave data from the captured ambient sound breaching a sound threshold;
 a storing unit configured to receive the trigger signal generated by the threshold unit, wherein the storing unit is configured to store, in response to receiving the trigger signal, a snippet of ambient light and/or a snippet of ambient sound captured around the time of receiving the trigger signal; and
 a review unit configured to review the stored snippets of ambient light and/or ambient sound to identify a root cause of the ambient light breaching the brightness threshold and/or the weighted audio wave data from the ambient sound breaching the sound threshold based on the stored snippets and to derive guidance information based on the identified root cause.

2. The system as claimed in claim 1, further comprising an overview camera configured to capture overview images including video data of an environment of the person, wherein the storing unit is configured to store in response to the received trigger signal, a snippet of the overview images captured around the time of receiving the trigger signal, and wherein the review unit is configured to allow reviewing stored snippets of the overview images in addition to the stored snippets of ambient light and/or ambient sound to identify the root cause of the ambient light breaching the brightness threshold and/or the ambient sound breaching the sound threshold based on the snippets of the overview images.

3. The system as claimed in claim 2, wherein the review unit is configured to automatically review the stored snippets of overview images in addition to stored snippets of ambient light and/or ambient sound to identify the root cause of the ambient light breaching the brightness threshold and/or the ambient sound breaching the sound threshold.

4. The system as claimed in claim 1, wherein the review unit is configured to automatically review the stored snippets of ambient light and/or ambient sound to identify the root cause of the ambient light breaching the brightness threshold and/or the ambient sound breaching the sound threshold.

5. The system as claimed in claim 1, wherein the weighting applied by the sound processor is based upon a sound frequency profile of a fetus in a womb.

6. The system as claimed in claim 1, further comprising a light processor configured to process the captured images before checking if the light level of the captured images breaching a light threshold by the threshold unit by applying a weighting representing a human eye sensitivity of a person of similar age as the monitored person.

7. The system as claimed in claim 1, further comprising an image processor configured to process the captured images before checking if the light level of the captured images breaches a light threshold by the threshold unit, wherein the image processor is configured to:
select a region of interest in an image, of the captured images, that includes or is adjacent to the eyes of the person; and
derive a brightness measure of the region of interest by selecting an intensity average of pixels in the region of interest or selecting an intensity of a brightest pixel, wherein the brightness measure is used as the brightness threshold.

8. The system as claimed in claim 1, further comprising an alarm unit configured to generate an alarm responsive to the brightness of the captured ambient light breaching the brightness threshold and/or responsive to the sound level of the captured ambient sound breaching the sound threshold.

9. The system as claimed in claim 1, further comprising a stress level processor configured for determining a stress level of the person, wherein the storing unit is configured to store in response to the received trigger signal, a snippet of the stress level information of the person captured around the time of receiving the trigger signal, and wherein the review unit is configured to allow reviewing the stored snippets of stress level information in addition to the stored snippets of ambient light and ambient sound to identify the root cause of the ambient light breaching the brightness threshold and ambient sound stored breaching the sound threshold based on the snippet of the stress level information.

10. The system as claimed in claim 9, further comprising a remote photo-plethysmographic processor configured to derive vital signs of the person from the captured images for use by the stress level processor for determining the stress level of the person.

11. A method of monitoring light and sound impact on a person, comprising:
capturing ambient light at an area where the person is located over time, wherein the light capturing unit comprises a camera configured to capture images of the area, and wherein capturing ambient light comprises determining, with one or more processors, an ambient light brightness of the captured ambient light from a segment of the image containing at least the eyes of the person;
capturing ambient sound at the area where the person is located over time;
processing audio wave data from the captured ambient sound, wherein processing comprises applying a weighting to the audio wave data based upon a spectral hearing sensitivity of a person of similar age as the monitored person;
generating and issuing a trigger signal responsive to the brightness of the captured ambient light breaching a brightness threshold and/or responsive to a sound level of the weighted audio wave data from the captured ambient sound breaching a sound threshold;
storing, in response to receiving the trigger signal trigger signal generated by the threshold unit, a snippet of ambient light and/or a snippet of ambient sound captured around the time of receiving the trigger signal; and
reviewing the stored snippets of ambient light and ambient sound to identify a root cause of the ambient light breaching the brightness threshold and/or the weighted audio wave data from the ambient sound breaching the sound threshold based on the stored snippets and to derive guidance information based on the identified root cause.

12. A device for monitoring light and sound impact on a person, comprising:
a light sensing unit configured to capture captures ambient light at an area where the person is located the person over time, wherein the light sensing unit comprises a camera configured to capture images of the area, and wherein the light sensing unit comprises one or more processors configured to determine an ambient light brightness of the captured ambient light from a segment of the image containing at least the eyes of the person;
a sound sensing unit configured to capture ambient sound at the area where the person is located over time;
a sound processor configured to process audio wave data from the captured ambient sound, the sound processor applying a weighting to the audio wave data based upon a spectral hearing sensitivity of a person of similar age as the monitored person;
a threshold unit configured to generate and issue a trigger signal responsive to the brightness of the captured ambient light breaching a brightness threshold and/or responsive to a sound level of the weighted audio wave data from the ambient sound captured at the area where the person is located over time breaching a sound threshold;

a storing unit configured to store, in response to the received trigger signal, snippets of ambient light and/or ambient sound captured around the time of receiving the trigger signal; and a review unit configured to review the stored snippets of ambient light and/or ambient sound to identify a root cause of the ambient light breaching the brightness threshold and/or ambient sound breaching the sound threshold based on the stored snippets and to derive guidance information based on the identified root cause.

13. A method of monitoring light and sound impact on a person, comprising:

capturing, with a camera, images of an area where the person is located over time;

determining, with one or more processors, an ambient light brightness of the captured ambient light from a segment of the image containing at least the eyes of the person;

capturing, with a sound sensor, ambient sound signals at the area where the person is located over time;

processing, with a sound processor, audio wave data from the captured ambient sound by applying a weighting to the audio wave data based upon a spectral hearing sensitivity of a person of similar age as the monitored person;

generating and issuing a trigger signal responsive to the brightness of the ambient light breaching a brightness threshold and/or responsive to a sound level of the weighted audio wave data from the ambient sound captured at an area where the person is located over time breaching a sound threshold;

storing, in response to the received trigger signal, snippets of ambient light and/or ambient sound captured around the time of receiving the trigger signal; and reviewing the stored snippets of ambient light and/or ambient sound to identify a root cause of the ambient light breaching the brightness threshold and/or the weighted audio wave data from the ambient sound breaching the sound threshold based on the stored snippets and to derive guidance information based on the identified root cause.

14. A computer readable non-transitory medium having instructions stored thereon which, when carried out on a computer, cause the computer to perform the following steps of the method as claimed in claim 13.

15. A system for monitoring light and sound impact on a person, comprising:

a light sensor configured to capture ambient light at an area where the person is located over time, wherein the light sensor comprises a camera configured to capture images of the area, and wherein the light sensor comprises one or more processors configured to determine an ambient light brightness of the captured ambient light from a segment of the image containing at least the eyes of the person;

a sound sensor configured to capture ambient sound at an area where the person is located over time;

a sound processor configured to process audio wave data from the captured ambient sound, the sound processor applying a weighting to the audio wave data based upon a spectral hearing sensitivity of a person of similar age as the monitored person;

a threshold sensor configured to generate and issue a trigger signal responsive to the brightness of the captured ambient light breaching a brightness threshold and/or responsive to a sound level of the weighted audio wave data from the captured ambient sound breaching a sound threshold;

a storage configured to store, in response to receiving the trigger signal trigger signal from the threshold sensor, snippets of ambient light and/or ambient sound captured around the time of receiving the trigger signal; and a processor configured to review the stored snippets of ambient light and ambient sound to identify a root cause of the ambient light breaching the brightness threshold and/or the weighted audio wave data from the ambient sound breaching the sound threshold based on the stored snippets and to derive guidance information based on the identified root cause.

* * * * *